United States Patent
Uto (10) Patent No.: US 12,239,416 B2
(45) Date of Patent: Mar. 4, 2025

(54) LIGHT THERAPY DIAGNOSTIC DEVICE AND METHOD FOR OPERATING THE SAME

(71) Applicant: KANEKA CORPORATION, Osaka (JP)

(72) Inventor: Toshihiko Uto, Settsu (JP)

(73) Assignee: KANEKA CORPORATION, Osaka (JP)

( * ) Notice: Subject to any disclaimer, the term of this patent is extended or adjusted under 35 U.S.C. 154(b) by 515 days.

(21) Appl. No.: 17/617,058

(22) PCT Filed: Jun. 2, 2020

(86) PCT No.: PCT/JP2020/021776
§ 371 (c)(1),
(2) Date: Dec. 7, 2021

(87) PCT Pub. No.: WO2020/250752
PCT Pub. Date: Dec. 17, 2020

(65) Prior Publication Data
US 2022/0330829 A1   Oct. 20, 2022

(30) Foreign Application Priority Data
Jun. 12, 2019   (JP) ................... 2019-109902

(51) Int. Cl.
*A61B 5/00* (2006.01)
*A61N 5/06* (2006.01)
*A61N 5/067* (2006.01)

(52) U.S. Cl.
CPC .......... *A61B 5/0084* (2013.01); *A61B 5/0062* (2013.01); *A61N 5/062* (2013.01); *A61N 2005/0632* (2013.01); *A61N 5/067* (2021.08)

(58) Field of Classification Search
CPC ............ A61N 5/062; A61N 2005/0632; A61N 2005/0665; A61N 2005/0666; A61N 5/067; A61B 5/0084; A61B 5/0062
(Continued)

(56) References Cited

U.S. PATENT DOCUMENTS 3,858,577 A      1/1975  Bass et al.
5,693,043 A  *  12/1997  Kittrell .............. A61B 1/00096
                                                        606/15
(Continued)

FOREIGN PATENT DOCUMENTS

JP    2008125939 A  *  6/2008  ........... G01N 21/898
JP    2014-104138 A     6/2014

OTHER PUBLICATIONS

International Search Report, issued in PCT/JP2020/021776, dated Aug. 4, 2020.
(Continued)

*Primary Examiner* — Ahmed M Farah
(74) *Attorney, Agent, or Firm* — Birch, Stewart, Kolasch & Birch, LLP (57) ABSTRACT

A light therapy diagnostic device comprising a shaft, and an optical waveguide disposed in a lumen of the shaft and being movable forward and backward in a longitudinal direction, wherein: the optical waveguide guides a first light and a second light; the shaft has a lateral emission window which allows the first light and the second light to be emitted toward a lateral direction and a distal emission window which allows the first light to be emitted toward a distal direction; a first mirror is provided on a distal end part of the optical waveguide and reflects the first light toward a lateral direction of the shaft; and a second mirror is provided on an inner surface of the shaft, located distal to a distal end of the
(Continued)

lateral emission window, and reflects the first light reflected by the first mirror toward a distal direction of the shaft.

16 Claims, 6 Drawing Sheets

(58) Field of Classification Search
USPC .......................................................... 607/88
See application file for complete search history.

(56) References Cited

U.S. PATENT DOCUMENTS

| | | |
|---|---|---|
| 10,539,731 B2 | 1/2020 | Le et al. |
| 10,631,930 B1 | 4/2020 | Miyagawa et al. |
| 2006/0287595 A1 | 12/2006 | Maschke |
| 2009/0124958 A1 | 5/2009 | Li et al. |
| 2010/0111118 A1 | 5/2010 | Seo et al. |
| 2011/0275890 A1* | 11/2011 | Wang .................... A61B 8/4461 600/104 |
| 2016/0374562 A1* | 12/2016 | Vertikov ............... A61B 5/0095 600/424 |
| 2017/0224420 A1 | 8/2017 | Stringer et al. |
| 2017/0326382 A1 | 11/2017 | Seymour et al. |
| 2020/0093365 A1* | 3/2020 | Wu ........................ G02B 6/262 |
| 2020/0297970 A1* | 9/2020 | Hamm ............... A61B 5/02007 |
| 2022/0161046 A1* | 5/2022 | Tsukamoto ....... A61M 25/0043 |
| 2022/0226665 A1* | 7/2022 | Uto ...................... A61B 1/0607 |

OTHER PUBLICATIONS

International Search Report, issued in PCT/JP2020/021777, dated Aug. 11, 2020.
Written Opinion of the International Searching Authority, issued in PCT/JP2020/021776, dated Aug. 4, 2020.
Written Opinion of the International Searching Authority, issued in PCT/JP2020/021777, dated Aug. 11, 2020.

\* cited by examiner

LIGHT THERAPY DIAGNOSTIC DEVICE AND METHOD FOR OPERATING THE SAME

TECHNICAL FIELD

The present invention relates to a light therapy diagnostic device used for a treatment method using light such as a photodynamic therapy (PDT) and photo-immunotherapy (PIT) and a method for operating the same.

BACKGROUND ART

Biomedical treatment methods using light such as PDT and PIT are attracting attention, and as described in the following patent literatures, optical measuring devices that are capable of emitting light for grasping a condition of a treatment site prior to the emission of the light for treatment in a living body are known.

Patent Literature 1 discloses an optical probe comprising a tubular probe outer cylinder, an optical waveguide member, a first irradiation unit, and a second irradiation unit. The optical waveguide member guides a first light and a second light disposed in an inner space of the probe outer cylinder in an axial direction of the probe outer cylinder. The first irradiation unit irradiates the first light emitted from a tip of the optical waveguide member while scanning on an irradiation target placed outside the probe outer cylinder. The second irradiation unit enables the second light emitted from the tip of the optical waveguide member to be irradiated on the irradiation target placed outside the prove outer cylinder and on a trajectory of the first light formed on the irradiation target when the first irradiation unit irradiates while scanning. When the first light and the second light are simultaneously emitted from the optical waveguide member, the first irradiation unit and the second irradiation unit irradiate the first light and the second light, respectively, to different parts on the irradiation target.

Patent Literature 2 discloses an endoscope system comprising an insertion part, an illumination light irradiation unit, a treatment light irradiation unit, a light receiving unit, and a light intensity detection unit. The insertion part is formed to have a tubular shape that can be inserted into a body cavity of a specimen. The illumination light irradiation unit is provided at a tip part of the insertion part, and is configured to irradiate illumination light for illuminating a subject in the body cavity forward of the tip part. The treatment light irradiation unit is provided integrally with or separately from the tip part, and includes a therapeutic light transmission unit that transmits therapeutic light supplied from a therapeutic light supply unit, and a light diffusing unit that diffuses and irradiates the therapeutic light transmitted by the therapeutic light transmission unit into an substantially tubular region forward of the tip part. The light receiving unit receives a return light of the illumination light emitted forward of the tip part and a return light of the therapeutic light emitted into the substantially tubular region forward of the tip part, respectively. The light intensity detection unit detects an intensity of the return light of the therapeutic light received by the light receiving unit.

CITATION LIST

Patent Literature

Patent Literature 1
Japanese Unexamined Laid-open Patent Application Publication No. 2008-125939
Patent Literature 2
Japanese Unexamined Laid-open Patent Application Publication No. 2014-104138

SUMMARY OF INVENTION

Technical Problem

Optical devices used in the apparatuses described in the above patent literatures are all very small in diameter, manufactured using microfabrication technologies such as MEMS, for example. Therefore, the amount of light tends to decrease both in illumination optics that illuminates a surface of a living body and in light receiving optics that receives light returned from the surface of the living body, and there is room for improvement in increasing resolution of an observation image. An object of the present invention is to provide a light therapy diagnostic device that reduces the loss due to reduction in the amount of the light used for biological observation, such as, for example, vignetting and aperture eclipse, and that improves efficiency of light utilization, and a method for operating thereof.

Solution to Problem

One embodiment of the light therapy diagnostic device of the present invention that has achieved the above object is a light therapy diagnostic device comprising: a catheter shaft having a first end and a second end in a longitudinal direction and a lumen extending in the longitudinal direction; and an optical waveguide disposed in the lumen of the catheter shaft and being movable forward and backward in the longitudinal direction; wherein: the optical waveguide guides a first light and a second light having a wavelength different from that of the first light; the catheter shaft has a lateral emission window located on a lateral part of the catheter shaft and a distal emission window located on a distal end part of the catheter shaft; the lateral emission window allows the first light and the second light to be emitted toward a lateral direction; the distal emission window allows the first light to be emitted toward a distal direction; a first mirror is provided on a distal end part of the optical waveguide and reflects the first light toward a lateral direction of the catheter shaft; and a second mirror is provided on an inner surface of the catheter shaft, located distal to a distal end of the lateral emission window, and reflects the first light reflected by the first mirror toward a distal direction of the catheter shaft. Since the above light therapy diagnostic device is configured to be provided with the second mirror which is disposed on the inner surface of the catheter shaft, located distal to a distal end of the lateral emission window, and reflects the first light reflected by the first mirror toward a distal direction of the catheter shaft, efficiency of light utilization can be improved by reducing the loss due to reduction in the amount of the light used for biological observation while having an optical system for light therapy.

In the above light therapy diagnostic device, it is preferable that the lateral emission window is disposed over an entire circumference of the catheter shaft, and the second mirror is disposed over an entire circumference of the inner surfaces of the catheter shaft.

In the above light therapy diagnostic device, it is preferable that a proximal part of the optical waveguide is connected to a circumferential rotating member that rotates the optical waveguide in a circumferential direction of the catheter shaft.

In the above light therapy diagnostic device, it is preferable that the optical waveguide includes a first core, a second core disposed outside the first core, and a clad disposed outside the second core, and a refractive index n1 of the first core, a refractive index n2 of the second core, and a refractive index n3 of the clad satisfy the relationship of $n1>n2>n3$.

In the above light therapy diagnostic device, it is preferable that the optical waveguide includes an intermediate clad disposed outside the first core and inside the second core, and the refractive index n1 of the first core, the refractive index n2 of the second core, and a refractive index n4 of the intermediate clad satisfy the relationship of $n1>n2>n4$.

In the above light therapy diagnostic device, it is preferable that the lateral emission window is located at a position corresponding to a non-existent area of the clad.

In the above light therapy diagnostic device, it is preferable that the second core has a light diffusion region disposed proximal to the first mirror.

In the above light therapy diagnostic device, it is preferable that surface roughness Ra of an outer surface of the second core in the light diffusion region is larger than surface roughness Ra of an outer surface of the second core in a distal region located distal to the light diffusion region, wherein the surface roughness Ra is determined based on an arithmetic average roughness Ra specified in JIS B 0601 (2001).

In the above light therapy diagnostic device, it is preferable that the second core contains light diffusing particles in the light diffusion region.

In the above light therapy diagnostic device, it is preferable that a normal of a distal end surface of the first core is inclined with respect to an optical axis of the optical waveguide, and a metal material is disposed on the distal end surface of the first core.

In the above light therapy diagnostic device, it is preferable that a distal end part of the catheter shaft is sharpened.

It is preferable that the above light therapy diagnostic device further comprises a light source that generates the first light, and a lens disposed between the light source and the first mirror.

In the above light therapy diagnostic device, it is preferable that an aberration correction lens is disposed distal to the second mirror.

In the above light therapy diagnostic device, it is preferable that the catheter shaft includes a balloon connected to the lumen thereof.

The present invention also provides a method for operating the above light therapy diagnostic device. One embodiment of a method for operating the light therapy diagnostic device of the present invention comprising the steps of: guiding the first light to the optical waveguide; guiding the second light to the optical waveguide to emit the second light from the lateral emission window, after guiding the first light to the optical waveguide; and guiding the first light to the optical waveguide, after emitting the second light from the lateral emission window.

Advantageous Effects of Invention

According to the above light therapy diagnostic device and its operating method, it is possible to reduce the loss due to reduction in the amount of light used for biological observation while having an optical system for light therapy, and improve efficiency of light utilization.

DESCRIPTION OF EMBODIMENTS

Hereinafter, the present invention is specifically explained below based on the following embodiments; however, the present invention is not restricted by the embodiments described below of course, and can be certainly put into practice after appropriate modifications within in a range meeting the gist of the above and the below, all of which are included in the technical scope of the present invention. In the drawings, hatching or a reference sign for a member may be omitted for convenience, and in such a case, the description and other drawings should be referred to. In addition, sizes of various members in the drawings may differ from the actual sizes thereof, since priority is given to understanding the features of the present invention.

One embodiment of the light therapy diagnostic device of the present invention is a light therapy diagnostic device comprising: a catheter shaft having a first end and a second end in a longitudinal direction and a lumen extending in the longitudinal direction; and an optical waveguide disposed in the lumen of the catheter shaft and being movable in the longitudinal direction; wherein: the optical waveguide guides a first light and a second light having a wavelength different from that of the first light; the catheter shaft has a lateral emission window located on a lateral part of the catheter shaft and a distal emission window located on a distal end part of the catheter shaft; the lateral emission window allows the first light and the second light to be emitted toward a lateral direction; the distal emission window allows the first light to be emitted toward a distal direction; a first mirror is provided on a distal end part of the optical waveguide and reflects the first light toward a lateral direction of the catheter shaft; and a second mirror is provided on an inner surface of the catheter shaft, located distal to a distal end of the lateral emission window, and reflects the first light reflected by the first mirror toward a distal direction of the catheter shaft. Since the above light therapy diagnostic device is configured to be provided with the second mirror which is disposed on the inner surface of the catheter shaft, located distal to a distal end of the lateral emission window, and reflects the first light reflected by the first mirror toward a distal direction of the catheter shaft, efficiency of light utilization can be improved by reducing the loss due to reduction in the amount of light used for biological observation while having an optical system for light therapy.

Figure 1:
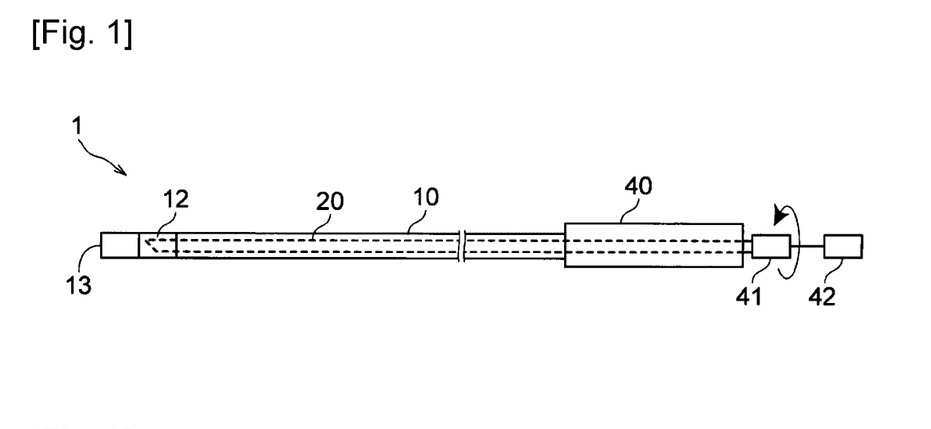
FIG. 1 shows a lateral view of a light therapy diagnostic device according to an embodiment of the present invention.
Figure 2:
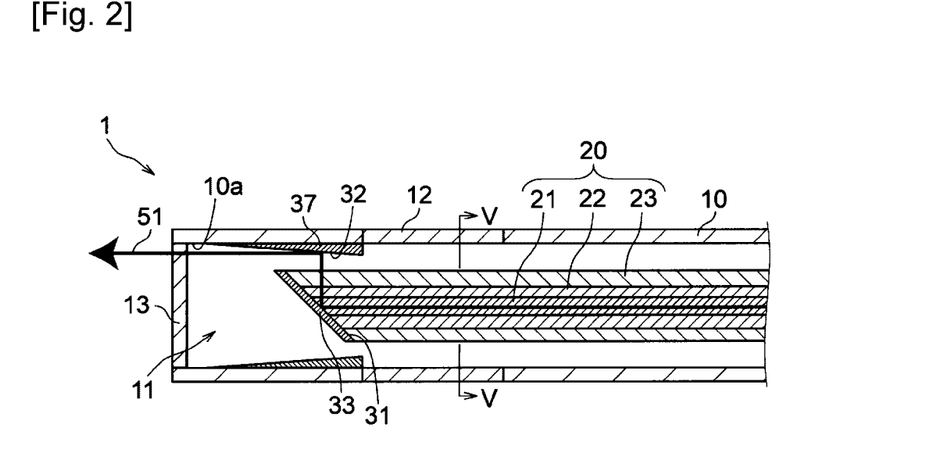
FIG. 2 shows an enlarged cross-sectional view of a distal part of the light therapy diagnostic device shown in FIG. 1, and shows a state in which a first light is emitted toward a distal direction of the catheter shaft.
Figure 3:
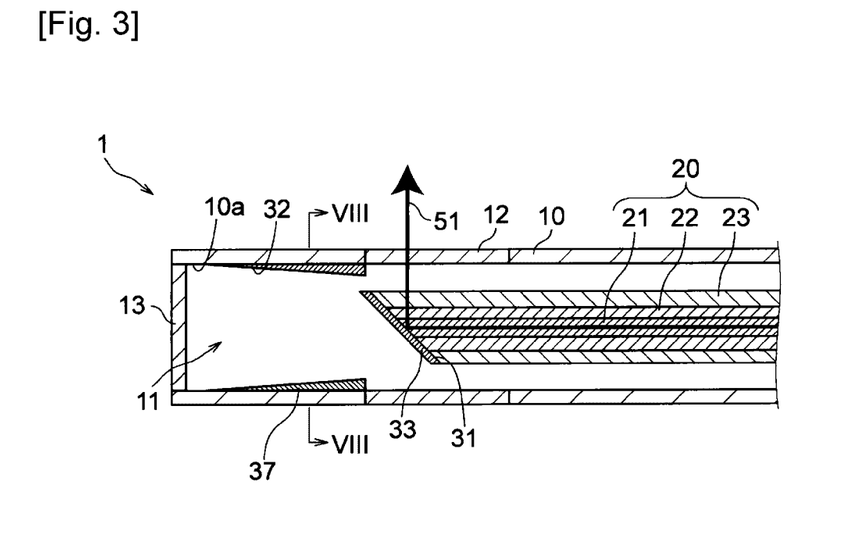
FIG. 3 shows an enlarged cross-sectional view of the distal part of the light therapy diagnostic device shown in FIG. 1, and shows a state in which a first light is emitted toward a lateral direction of the catheter shaft.
Figure 4:
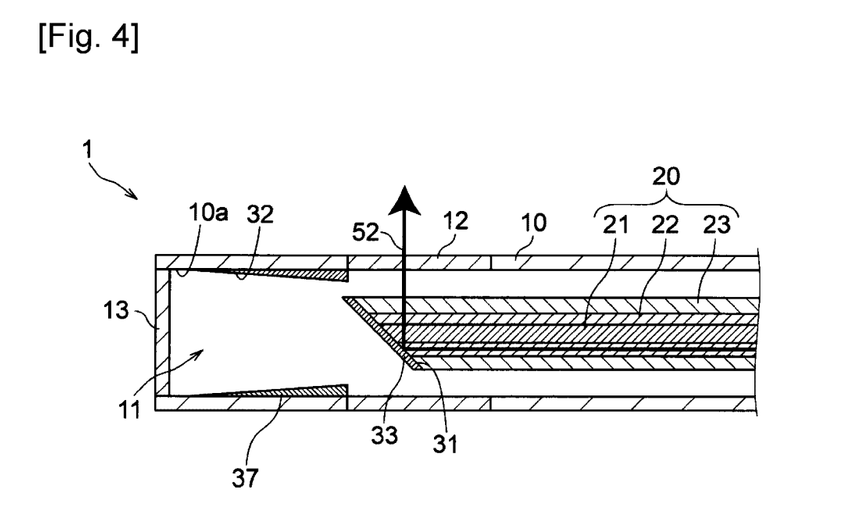
FIG. 4 shows an enlarged cross-sectional view of the distal part of the light therapy diagnostic device shown in FIG. 1, and shows a state in which a second light is emitted toward a lateral direction of the catheter shaft.

The configuration of the light therapy diagnostic device is explained with reference to FIGS. 1 to 4. FIG. 1 shows a lateral view of a light therapy diagnostic device according to an embodiment of the present invention, and FIGS. 2 to 4 show enlarged cross-sectional views of a distal part of the light therapy diagnostic device shown in FIG. 1. FIG. 2 represents a state in which a first light is emitted toward a distal direction of the catheter shaft, FIG. 3 represents a state in which a first light is emitted toward a lateral direction of the catheter shaft, and FIG. 4 represents a state in which a second light is emitted toward a lateral direction of the catheter shaft. A light therapy diagnostic device 1 comprises a catheter shaft 10 and an optical waveguide 20. Hereinafter, the light therapy diagnostic device 1 may be simply referred to as a device 1, and the catheter shaft 10 may be simply referred to as a shaft 10.

The device 1 can be used for PDT and PIT. In the device 1, an optical coherence tomography (OCT) method is preferably adopted for observing a living tissue by image diagnosis, however, an ultrasonic imaging method or a fluorescence imaging method may be adopted.

The shaft 10 has a first end and a second end that define a longitudinal direction. A distal side of the device 1 and the shaft 10 means a first end side in the longitudinal direction of the shaft 10 (in other words, a longitudinal axis direction of the shaft 10) and refers to a treatment target side. A proximal side of the light therapy diagnostic device 1 and the shaft 10 means a second end side in the longitudinal direction of the shaft 10 and refers to a hand side of a user (operator). In FIG. 1, the left side represents the distal side, and the right side represents the proximal side. Further, in a radial direction of the shaft 10, an inner side means a direction toward a center of the longitudinal axis of the shaft 10, and an outer side means a direction opposite to the inner side, namely a radiation direction.

The shaft 10 has a lumen 11 extending in the longitudinal direction. The shaft 10 has a tubular structure to dispose an optical waveguide 20 in the lumen 11. Since the shaft 10 is inserted into a body, it preferably has flexibility. Examples of the tubular structure of the shaft 10 include: a hollow body formed by arranging one or a plurality of wires in a certain pattern; the hollow body of which at least one of an inner surface and an outer surface thereof is coated with a resin; a cylindrical resin tube; and combination thereof (for example, those connected in the longitudinal direction of the shaft 10). As the hollow body in which wires are arranged in a certain pattern, a tubular body having a mesh structure by which wires are simply crossed or knitted, or a coil in which a wire is wound is exemplified. The wire may be one or a plurality of single wires, or may be one or a plurality of stranded wires. The resin tube can be manufactured, for example, by extrusion molding. In the case where the shaft 10 is made of a tubular resin tube, the shaft 10 can be composed of a single layer or a plurality of layers. A part of the shaft 10 in the longitudinal direction or a circumferential direction may be composed of a single layer, and another part of that may be composed of a plurality of layers. As shown in FIG. 1, a handle 40 gripped by an operator is preferably connected to a proximal part of the shaft 10. The device 1 may be incorporated in an endoscope or may be used as a combined device. This enables more detailed observation and treatment of a target site.

The shaft 10 can be composed of, for example, a synthetic resin such as a polyolefin resin (for example, polyethylene, polypropylene), a polyamide resin (for example, nylon), a polyester resin (for example, PET), an aromatic polyetherketone resin (for example, PEEK), a polyether polyamide resin, a polyurethane resin, a polyimide resin and a fluororesin (for example, PTFE, PFA, ETFE), or a metal such as stainless steel, carbon steel and nickel-titanium alloy. These may be used alone or in combination of two or more.

The optical waveguide 20 is disposed in the lumen 11 of the shaft 10 and can move forward and backward in the longitudinal direction of the shaft 10. The optical waveguide 20 guides a first light 51 and a second light 52 whose wavelengths are different from each other. Examples of the optical waveguide 20 include an optical fiber having a core and a clad. A light source is preferably connected to a proximal part of the optical waveguide 20. Thereby, the first light 51 and the second light 52 can enter the optical waveguide 20.

The shaft 10 has a lateral emission window 12 located on a lateral part of the shaft 10 and a distal emission window 13 located on a distal end part of the shaft 10. The lateral emission window 12 allows the first light 51 and the second light 52 to be emitted toward a lateral direction therefrom, and the distal emission window 13 allows the first light 51 to be emitted toward a distal direction therefrom. By providing the emission windows on the shaft 10 in this manner, the lights can be emitted from the emission windows. Further, the device 1 is provided with a first mirror 31 which is disposed on a distal end part of the optical waveguide 20 and reflects the first light 51 toward the lateral direction of the shaft 10, and a second mirror 32 which is disposed on an inner surface 10a of the shaft 10, located distal to a distal end of the lateral emission window 12, and reflects the first light 51 reflected by the first mirror 31 toward a distal direction of the shaft 10. Since the device 1 is configured to be provided with the second mirror 32 which is disposed on the inner surface 10a of the shaft 10, located distal to the distal end of the lateral emission window 12, and reflects the first light 51 reflected by the first mirror 31 toward a distal direction of the shaft 10, efficiency of light utilization can be improved by reducing the loss due to reduction in the amount of light used for biological observation while having an optical system for light therapy.

By moving the optical waveguide 20 in the lumen 11 of the shaft 10 in the longitudinal direction of the shaft 10, the position of the optical waveguide 20 relative to the shaft 10 can be changed. Thereby, a user can switch between a lateral observation mode, in which a lateral side of the device 1 is observed by emitting the first light 51 from the lateral emission window 12, and a forward observation mode, in which a front of the device 1 is observed by emitting the first light 51 from the distal emission window 13. When puncturing the device 1 into a body, the risk of the device 1 puncturing a blood vessel can be reduced by setting it to the forward observation mode. After inserting the device 1 to a predetermined position, a target site can be observed by setting it the lateral observation mode.

It is preferable that the first light 51 is an observation light for grasping a condition of a treatment site or its surrounding site, and the second light 52 is a treatment light. Thereby, both grasping a condition of a treatment site and providing treatment with one device 1 can be conducted, and it is possible to perform diagnosis and treatment at the same time, which has been difficult in the past. By observing a target area with the observation light after irradiation of the treatment light, the treatment result of the target area can be confirmed. As a result, the procedure time and treatment period can be shortened. As shown in FIG. 2, when the first light 51 reflected by the first mirror 31 and the second mirror 32 is emitted from the distal emission window 13 toward a distal direction, it becomes possible to grasp a condition of a living tissue on a distal side of the device 1. In OCT, a tomographic image is created based on the reflected light when the first light 51 is irradiated to a living tissue. As shown in FIG. 3, when the first light 51 reflected by the first mirror 31 is emitted from the lateral emission window 12 toward a lateral direction, it becomes possible to grasp a condition of a living tissue on a lateral side of the shaft 10. As shown in FIG. 4, when the second light 52 is emitted in the lateral direction from the lateral emission window 12 and is irradiated to a living tissue on a lateral side of the shaft 10, treatment of living using the light can be performed.

For the observation of a living tissue by OCT, the first light 51 is preferably near-infrared light, and more preferably infrared light. As a result, passability of the first light 51 to the living tissue is increased. The light source of the first light 51 may be a super luminescent diode light source, a super continuum light source, or a wavelength sweep laser. The wavelength (center wavelength) of the first light 51 may be, for example, 1.3 μm or longer, 1.35 μm or longer, or 1.4 μm or longer, and may also be allowable to be 1.8 μm or shorter, 1.75 μm or shorter, or 1.7 μm or shorter.

The second light 52 is preferably a laser beam which has a wavelength suitable for phototherapy such as PDT and PIT, and irradiates a living tissue. The wavelength of the second light 52 is preferably shorter than the wavelength of the first light 51. The wavelength of the second light 52 may be, for example, 0.64 μm or longer, 0.65 μm or longer, or 0.66 μm or longer, and may also be allowable to be 0.72 μm or shorter, 0.71 μm or shorter, or 0.7 μm or shorter.

The first light 51 and the second light 52 may be emitted from one light source, or the first light 51 and the second light 52 may be emitted from different light sources from each other.

Figure 7:
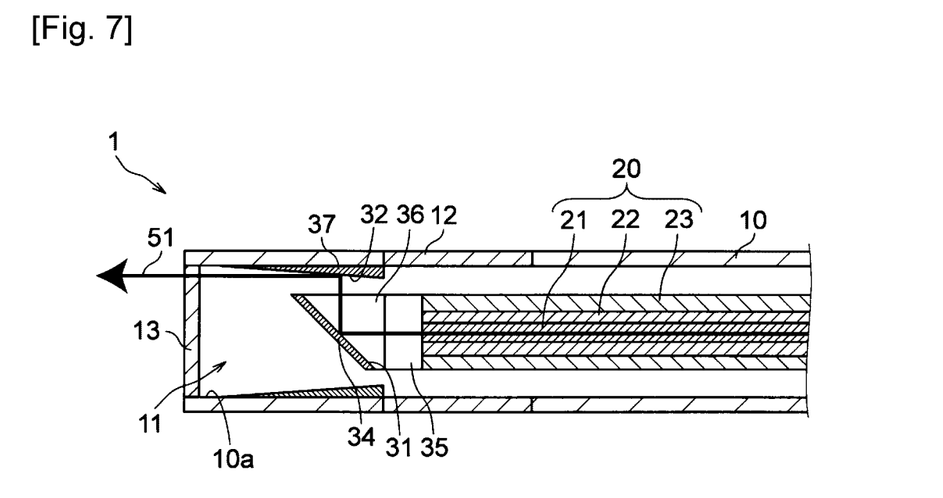
FIG. 7 shows a lateral cross-sectional view of a modified example of the light therapy diagnostic device of FIG. 2.

It is preferable that the device 1 comprises a light source 42 that generates the first light 51 and a lens disposed between the light source 42 and the first mirror 31. The first light 51 can enter the optical waveguide 20 by the light source 42 and the lens focuses the first light 51, whereby it is possible to obtain an image of a living tissue on a lateral side of the lateral emission window 12 or an image of a living tissue on a distal side of the distal emission window 13 with higher sensitivity. The lens may focus the first light 51 to be emitted to the living tissue, or may focus the first light 51 reflected by the living tissue. The lens may be located proximal to the optical waveguide 20, may be located in the optical waveguide 20, or may be located distal to the optical waveguide 20. As the lens, a so-called GRIN lens, which is composed of a continuously changing refractive index, is preferably used. FIG. 7, which is described below, shows an example of a GRIN lens (lens 35) disposed distal to the optical waveguide 20.

The lateral emission window 12 is preferably formed on a sidewall of the shaft 10. The lateral emission window 12 is preferably disposed so as to extend in a circumferential direction of the shaft 10, and more preferably disposed over an entire circumference of the shaft 10. Thereby, the second light 52 can be emitted over a wide area at once, so that a burden on a patient can be reduced.

The lateral emission window 12 is preferably located proximal to a distal end of the shaft 10. The proximal end of the lateral emission window 12 can be placed, for example, within 10 cm from the distal end of the shaft 10.

The distal emission window 13 is preferably formed on a distal end surface of the shaft 10. This makes it easier to emit the first light 51 toward a distal direction from the distal emission window 13. The distal end surface of the shaft 10 may be a flat surface or a curved surface. As a result, the distal emission window 13 can also be formed in a flat surface or a curved surface.

The lateral emission window 12 and the distal emission window 13 may be made of a material which the first light 51 or the second light 52 transmits. It is preferable that a constituent material of the lateral emission window 12 and the distal emission window 13 has a higher transmittance than a constituent material of a part of the shaft 10 where the emission window is not formed. Examples of a material constituting the lateral emission window 12 and the distal emission window 13 include, for example, synthetic resins such as (meth)acrylic resin (for example, polymethylmethacrylate (PMMA)), polycarbonate resin (for example, polydiethylene glycol bisallyl carbonate (PC)), polystyrene resin (for example, methyl methacrylate/styrene copolymer resin (MS), acrylonitrile styrene resin (SAN)), polyamide resin (for example, nylon), and polyolefin resin, in addition to a resin constituting the shaft 10. These may be used alone or in combination of two or more. The material constituting the lateral emission window 12 and the distal emission window 13 may be the same or different from each other.

Figure 5:
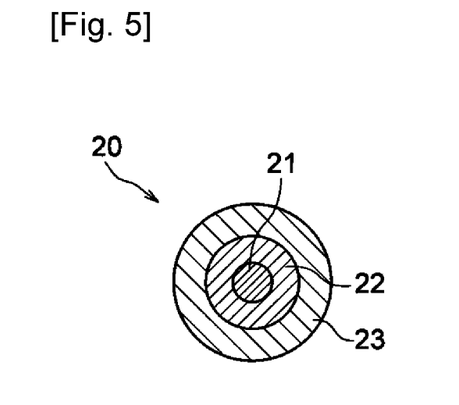
FIG. 5 shows a cross-sectional view taken along a line V-V of an optical waveguide shown in FIG. 2.

The configuration of the optical waveguide 20 is explained with reference to FIGS. 5 to 6. As shown in FIG. 5, the optical waveguide 20 preferably includes a first core 21, a second core 22 disposed outside the first core 21, and a clad 23 disposed outside the second core 22. Here, a refractive index n1 of the first core 21, a refractive index n2 of the second core 22, and a refractive index n3 of the clad 23 satisfy the relationship of n1>n2>n3. By disposing the second core 22 on an outer circumference of the first core 21 in this manner, the second light 52 can be easily emitted from the entire circumference of the shaft 10, so that it can be emitted over a wide range at once. The first core 21, the second core 22 and the clad 23 are preferably arranged concentrically. As a result, the first light 51 can be guided by the first core 21, and the second light 52 can be guided by the first core 21 and the second core 22, while the clad 23 prevents the lights from leaking.

The optical waveguide 20 may have one or more single-core fibers in which one core is disposed in one clad, or may have one or more multi-core fibers in which a plurality of cores are disposed in one clad. FIG. 5 shows an example of the optical waveguide 20 that is a multi-core fiber in which a plurality of cores 21 and 22 are disposed in one clad 23.

Figure 6:
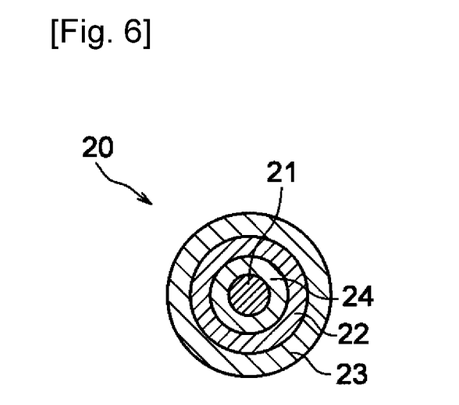
FIG. 6 shows a cross-sectional view of a modified example of the optical waveguide of FIG. 5.

FIG. 6 shows a cross-sectional view of a modified example of the optical waveguide 20 shown in FIG. 5. As shown in FIG. 6, the optical waveguide 20 preferably includes an intermediate clad 24 disposed outside the first core 21 and inside the second core 22. Here, the refractive index n1 of the first core 21, the refractive index n2 of the second core 22, and a refractive index n4 of the intermediate clad 24 satisfy the relationship of n1>n2>n4. Thereby, the light guided by the first core 21 can be confined by the intermediate clad 24, and the light guided by the second core 22 can be confined by the intermediate clad 24 and the clad 23. As a result, leakage of the light from the optical waveguide 20 can be prevented. The refractive index n4 of the intermediate clad 24 may be the same as or different from the refractive index n3 of the clad 23.

The first mirror 31 is provided to specular-reflect the first light 51 and the second light 52, and the second mirror 32 is provided to specular-reflect the first light 51. The first mirror 31 and the second mirror 32 may have a flat surface or a curved surface, respectively.

It is preferable that the first mirror 31 is inclined with respect to an optical axis of the optical waveguide 20. The inclination angle of the first mirror 31 with respect to the optical axis of the optical waveguide 20 may be 40 degrees or larger, 41 degrees or larger, or 42 degrees or larger, and may also be allowable to be 47 degrees or smaller, 46 degrees or smaller, or 45 degrees or smaller. By setting the inclination angle of the first mirror 31 in this manner, it becomes easy to totally reflect the first light 51 received by the first mirror 31. The first mirror 31 can be a reflective surface located at a distal end of the optical waveguide 20. The reflective surface of the first mirror 31 faces a proximal side of the shaft 10. A surface of a metal material can be used as the first mirror 31.

It is preferable that a normal of a distal end surface of the first core 21 is inclined with respect to the optical axis of the optical waveguide 20, and a metal material is disposed on a distal end surface of the first core 21. For example, a metal thin film 33 is formed on the distal end surface of the first core 21, and the surface of the metal thin film 33 can be used as the first mirror 31. In addition, the first mirror 31 can be inclined with respect to the optical axis of the optical waveguide 20, and thereby, the first mirror 31 can easily reflect the first light 51 or the second light 52. As a method of disposing a metal material on the distal end surface of the first core 21, vapor deposition, pasting of sheet-like metal piece, or the like can be employed.

FIG. 7 shows a lateral cross-sectional view of a modified example of the device 1 shown in FIG. 2. As shown in FIG. 7, a lens 35 for focusing the light such as a Gradient Index lens (GRIN lens) may be disposed between the optical waveguide 20 and the first mirror 31. By focusing the emitted light and the reflected light of the first light 51 using the lens 35, an image of a living tissue on the distal side of the distal emission window 13 can be obtained.

As shown in FIG. 7, it is preferable that a prism 36 is disposed on a distal side of the optical waveguide 20 (preferably on a distal side of the focusing lens 35) and a normal of a distal end surface of the prism 36 is inclined with respect to the optical axis of the optical waveguide 20. Thereby, the distal end surface of the prism 36 can be used as the first mirror 31. A metal thin film 34 can be placed on the distal end surface of the prism 36, and the surface of the metal thin film 34 can be used as the first mirror 31.

Figure 8:
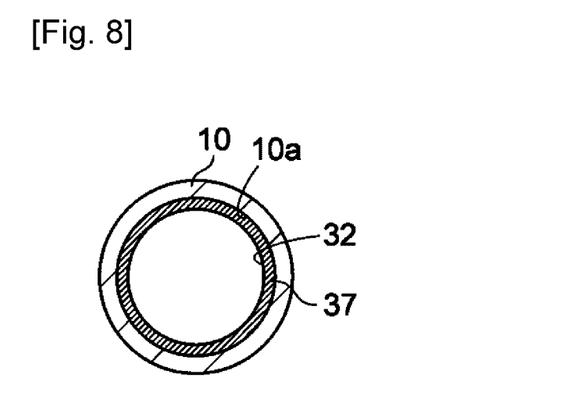
FIG. 8 shows a cross-sectional view of VIII-VIII of the light therapy diagnostic device shown in FIG. 3.

As shown in FIG. 8, it is preferable that the second mirror 32 is disposed over an entire circumference of the inner side surface 10a of the shaft 10. Thereby, the first light 51 reflected by the first mirror 31 can be received at any position in the circumferential direction. As a result, the second mirror 32 easily reflect the first light 51 from the first mirror 31 toward the distal direction of the shaft 10 without leakage.

Examples of the second mirror 32 include a surface of a metal thin film 37 formed on the inner surface 10a of the shaft 10. As a method of forming the metal thin film 37 on the inner surface 10a of the shaft 10, a method of injecting silver nitrate solution and a reducing agent solution into the lumen 11 of the shaft 10 and reducing silver to deposit on the inner surface 10a of the shaft 10 is mentioned.

In the case where the second mirror 32 is the surface of the metal thin film 37, the metal thin film 37 is formed so as to become thinner toward a distal side of the shaft 10, whereby the second mirror 32 can be formed to be inclined with respect to the optical axis of the optical waveguide 20. In that case, the second mirror 32 come to be formed in a truncated cone shape.

It is preferable that the second mirror 32 is inclined with respect to the optical axis of the optical waveguide 20. The inclination angle of the second mirror 32 with respect to the optical axis of the optical waveguide 20 may be 3 degrees or larger, 5 degrees or larger, or 10 degrees or larger, and may also be allowable to be 30 degrees or smaller, 25 degrees or smaller, or 15 degrees or smaller. By setting the inclination angle of the second mirror 32 in this manner, the first light 51 received on the second mirror 32 can be easily reflected toward the distal direction of the shaft 10.

It is preferable that the second mirror 32 is disposed distal to the lateral emission window 12. As a result, the second mirror 32 does not interference with the emission of the second light 52 from the lateral emission window 12.

It is preferable that the second mirror 32 is formed longer in the longitudinal direction of the shaft 10 than the first mirror 31. As a result, the first mirror 31 and the second mirror 32 tend to overlap with each other in a wide range in the longitudinal direction of the shaft 10.

The inclination angle of the first mirror 31 with respect to the optical axis of the optical waveguide 20 and the inclination angle of the second mirror 32 with respect to the optical axis of the optical waveguide 20 may be the same or different from each other; however, it is preferable that the inclination angle of the first mirror 31 Is larger than the inclination angle of the second mirror 32.

Examples of a metal constituting the first mirror 31 or the second mirror 32 include, for example, aluminum, silver, copper, tin, and a combination thereof. The material constituting the first mirror 31 and the second mirror 32 may be the same or different from each other.

Figure 9:
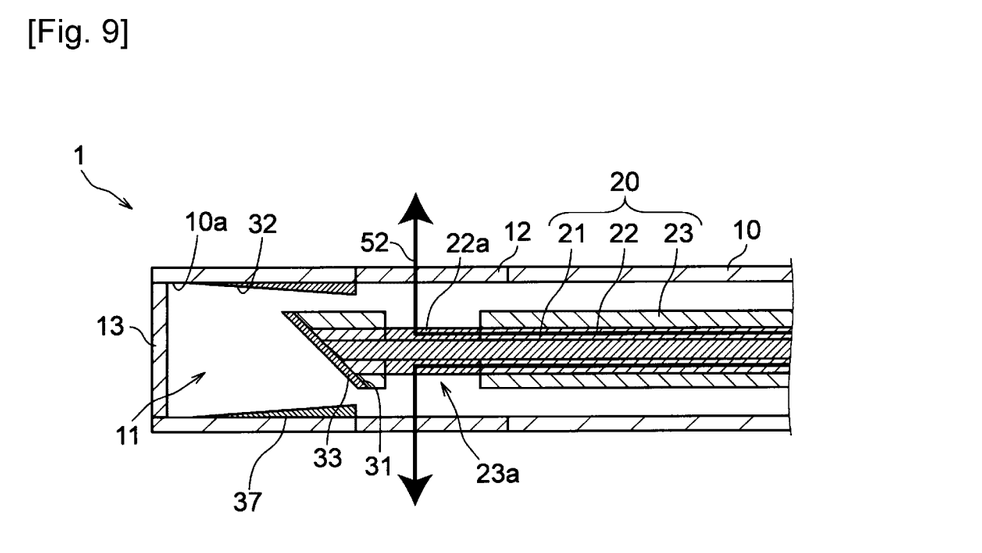
FIG. 9 shows a cross-sectional view of a modified example of the light therapy diagnostic device of FIG. 4.

FIG. 9 shows a cross-sectional view of a modified example of FIG. 4. As shown in FIG. 9, the lateral emission window 12 is preferably located at a position corresponding to a non-existing region 23a of the clad 23. Thereby, the first light 51 or the second light 52 guided by the first core 21 or the second core 22 can be emitted toward the lateral direction from the non-existing region 23a of the clad 23. Specifically, it is preferable that the second light 52 is emitted toward the lateral direction from the non-existing region 23a of the clad 23. That the lateral emission window 12 is located at a position corresponding to the non-existing region 23a of the clad 23 means that the non-existing region 23a of the clad 23 and the lateral emission window 12 of the shaft 10 overlaps with each other at least in part when the optical waveguide 20 is located at a certain position of the shaft 10.

The non-existing region 23a of the clad 23 is a region in which the core (the first core 21 or the second core 22, preferably the second core 22) inside the clad 23 is exposed to the outside due to the absence of the clad 23. Examples of a method of forming the non-existing region 23a of the clad 23 in this manner include a method of mechanically or chemically removing the clad 23, and for example, laser processing and etching processing are mentioned.

The non-existing region 23a of the clad 23 is preferably disposed so as to extend in the circumferential direction, and more preferably disposed over the entire circumference of the optical waveguide 20. Thereby, the second light 52 can be emitted over a wide area at once.

As shown in FIG. 9, the second core 22 preferably has a light diffusion region 22a proximal to the first mirror 31. By providing the light diffusion region 22a in the second core 22 in this manner, the second light 52 can be suitably diffused, so that the second light 52 can be emitted over a wide range at once.

It is preferable that the surface roughness Ra of an outer surface of the second core 22 in the light diffusion region 22a is larger than the surface roughness Ra of an outer surface of the second core 22 in a distal region distal to the light diffusion region 22a. Here, the surface roughness Ra is determined based on an arithmetic average roughness Ra specified in JIS B 0601 (2001). By setting the surface roughness in this manner, the second light 52 can be efficiently diffused from the light diffusion region 22a, so that it can be emitted over a wide range at once.

Examples of a method of roughening the outer surface of the second core 22 in the light diffusion region 22a include a method of mechanically or chemically roughening the surfaces, and for example, etching, blasting, scribing, wire-brushing, a method of using sandpaper, and the like are mentioned.

It is preferable that the second core 22 contains light diffusing particles in the light diffusion region 22a. Thereby, the second light 52 can be efficiently diffused in the light diffusion region 22a, so that it can be emitted over a wide range at once. Examples of the light diffusing particles include inorganic particles such as titanium oxide, barium sulfate and calcium carbonate, and organic particles such as crosslinked acrylic particles and crosslinked styrene particles.

It is preferable that the length of the light diffusion region 22a of the second core 22 or the length of the non-existing region 23a of the clad 23 in the longitudinal direction of the shaft 10 is shorter than that of the lateral emission window 12. This makes it easier to emit the second light 52 toward the lateral direction of the shaft 10 without loss.

As shown in FIGS. 2 to 4, it is preferable that a distal end of the shaft 10 is closed. Thereby, liquids such as body fluids are prevented from entering the lumen 11 of the shaft 10. A normal of a distal end surface of the shaft 10 may be parallel to the optical axis of the optical waveguide 20.

Although it is not shown in the drawings, the shaft 10 may be composed of a plurality of members. For example, the shaft 10 may include a cylindrical shaft body having an opening at a distal end thereof, and a cap provided at a distal end part of the shaft body and closing the opening of the shaft body. In that case, the distal emission window 13 may be formed on the cap. Thereby, a part of the distal emission window 13 and the shaft 10, where the emission window is not formed, can be easily composed of a different material. Regarding a material constituting the cap, the description of the constituent material of the shaft 10 can be referred to.

Figure 10:
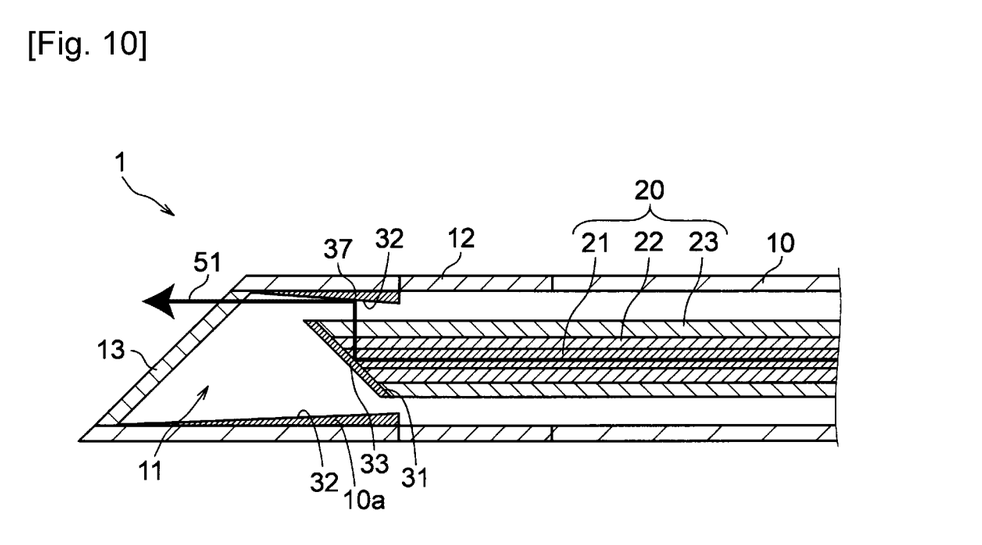
FIG. 10 shows a cross-sectional view of another modified example of the light therapy diagnostic device of FIG. 2.

FIG. 10 shows a cross-sectional view of a modified example of the device 1 of FIG. 2. As shown in FIG. 10, in a cross section along the longitudinal direction of the shaft 10, a distal end part of the shaft 10 may be formed in a sharp shape formed by one line or may be formed in a sharp shape formed by two or more lines. A distal end of the shaft 10 may be located at an outer end of the shaft 10 in a radial direction or may be located at a center of the longitudinal axis of the shaft 10. In this manner, it is preferable that the distal end part of the shaft 10 is sharpened. Since the distal end part of the shaft 10 can be punctured into a tissue, a position of the shaft 10 in a body can be fixed. As a result, it becomes easy to emit the first light 51 and the second light 52 for image diagnosis and treatment.

As shown in FIG. 1, a proximal part of the optical waveguide 20 is preferably connected to a circumferential rotating member 41 that rotates the optical waveguide 20 in the circumferential direction of the shaft 10. More preferably, the optical waveguide 20 rotates with respect to the shaft 10 around its optical axis. Since the optical waveguide 20 can be rotated around its optical axis, the emission position of the light from the lateral emission window 12 in the circumferential direction of the shaft 10 can be adjusted.

Figure 11:
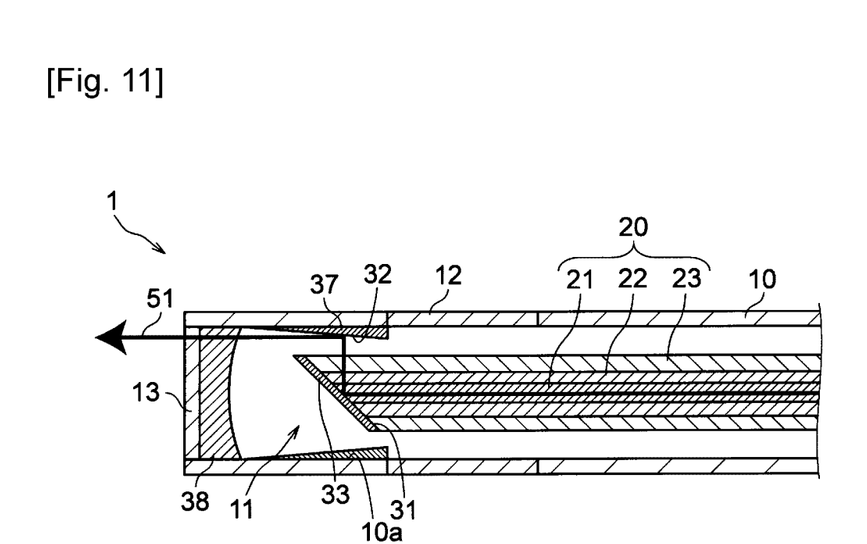
FIG. 11 shows a cross-sectional view of still another modified example of the light therapy diagnostic device of FIG. 2.

FIG. 11 shows a cross-sectional view of still another modification example of FIG. 2. As shown in FIG. 11, it is preferable that an aberration correction lens 38 is disposed distal to the second mirror 32 (more preferably, distal to a distal end of the second mirror 32). Since aberration generated by the reflection of the first light 51 onto the first mirror 31 and the second mirror 32 can be corrected, image formation is made easier and observation of a distal side of the shaft 10 is easily conducted. In particular, in the case where the second mirror 32 is formed in a truncated cone shape, the aberration correction lens 38 is preferably provided. Examples of the aberration correction lens 38 include a doublet lens in which a convex lens and a concave lens are combined, and an aspherical lens. One or more aberration correction lenses 38 can be disposed.

Although it is not shown in the drawings, the shaft 10 may be provided with a balloon on a distal part thereof. In particular, the shaft 10 may include a balloon connected to the lumen thereof. The balloon may be located so as to cover the lateral emission window 12 or may be located distal to or proximal to the lateral emission window 12, in relation to the lateral emission window 12 provided on the shaft 10. Alternatively, the balloon may cover the distal emission window 13 or both the lateral emission window 12 and the distal emission window 13. It is preferable that the balloon is attached to the shaft 10 so that an attaching part of the balloon to the shaft 10 does not overlap with the lateral emission window 12 and the distal emission window 13. In the case where the light can pass through the balloon, the balloon may be attached to the shaft 10 so as to overlap with the lateral emission window 12. By providing the balloon on the shaft 10, the device 1 can be fixed in a body cavity, and the light can be stably emitted from the lateral emission window 12. In the case where the balloon is arranged on the shaft 10 so as to cover the lateral emission window 12, the balloon is preferably made of a highly transparent material to prevent attenuation of the light emitted from the lateral emission window 12.

Each of the above preferred embodiments can be combined as necessary to form a part of the configuration of the light therapy diagnostic device of the present invention.

The present invention also provides a method for operating the above light therapy diagnostic device 1. One embodiment of the method for operating the light therapy diagnostic device 1 of the present invention comprises steps of: guiding the first light 51 to the optical waveguide 20; guiding the second light 52 to the optical waveguide 20 to emit the second light 52 from the lateral emission window 12, after guiding the first light 51 to the optical waveguide 20; and guiding the first light 51 to the optical waveguide 20, after emitting the second light 52 from the lateral emission window 12.

The optical waveguide 20 is moved distally with respect to the shaft 10 to a position where the first mirror 31 overlaps with the second mirror 32 in the longitudinal direction of the shaft 10. Specifically, the optical waveguide 20 is moved so that a distal end of the first mirror 31 is positioned distal to a proximal end of the second mirror 32.

The first light 51 is guided to the optical waveguide 20. As a result, the first light 51 is reflected by the first mirror 31 and the second mirror 32, and the first light 51 is emitted from the distal emission window 13 toward the distal direction. Thereby, a distal side of the light therapy diagnostic device 1 can be observed.

The optical waveguide 20 is moved proximally with respect to the shaft 10 to a position where the first mirror 31 does not overlap with the second mirror 32 in the longitudinal direction of the shaft 10. Specifically, the optical waveguide 20 is moved so that the distal end of the first mirror 31 is positioned proximal to the proximal end of the second mirror 32. At this time, it is preferable that the non-existing region 23a of the clad 23 or the light diffusion region 22a of the second core 22 is placed so as to overlap with the lateral emission window 12 in the longitudinal direction of the shaft 10.

After the first light 51 is guided to the optical waveguide 20, the second light 52 is guided to the optical waveguide 20 and the second light 52 is emitted from the lateral emission window 12. As a result, the second light 52 is reflected by the first mirror 31, and the second light 52 is emitted from the lateral emission window 12 toward the lateral direction of the shaft 10. Thereby, the second light 52 can be emitted to a tissue located on a lateral side of the shaft 10.

After the second light 52 is emitted from the lateral emission window 12, the first light 51 is guided to the optical waveguide 20. As a result, the first light 51 is reflected by the first mirror 31, and the first light 51 is emitted from the lateral emission window 12 toward the lateral direction of the shaft 10. Thereby, a state of the tissue located on the lateral side of the catheter can be grasped.

This application claims priority to Japanese Patent Application No. 2019-109902, filed on Jun. 12, 2019. All of the contents of the Japanese Patent Application No. 2019-109902, filed on Jun. 12, 2019, are incorporated by reference herein.

REFERENCE SIGNS LIST

1: light therapy diagnostic device
10: catheter shaft
10a: inner surface
11: lumen
12: lateral emission window
13: distal emission window
20: optical waveguide
21: first core
22: second core
22a: light diffusion region
23: clad
23a: non-existent region of clad
24: intermediate clad
31: first mirror
32: second mirror
33, 34: metal thin film
35: lens
36: prism
37: metal thin film
38: aberration correction lens
40: handle
41: circumferential rotating member
42: light source
51: first light
52: second light

The invention claimed is:

1. A light therapy diagnostic device comprising:
a shaft having a distal end and a proximal end in a longitudinal direction and a lumen extending in the longitudinal direction; and
an optical waveguide disposed in the lumen of the shaft such that the optical waveguide is movable forward and backward in the longitudinal direction; wherein:
the optical waveguide guides a first light and a second light;
the shaft has a lateral emission window located on a lateral part of the shaft and a distal emission window located on a distal end part of the shaft;
the lateral emission window is configured to allow the first light and the second light to be emitted from the optical waveguide toward a lateral direction;
the distal emission window is configured to allow the first light to be emitted from the optical waveguide toward a distal direction;
a first mirror is provided on a distal end part of the optical waveguide such that the first mirror reflects the first light toward a lateral direction of the shaft; and
a second mirror is provided on an inner surface of the shaft, located distal to a distal end of the lateral emission window, such that the second mirror reflects the first light reflected by the first mirror toward the distal end of the shaft.

2. The light therapy diagnostic device according to claim 1, wherein
the lateral emission window is disposed on the lateral part of the shaft such that the lateral emission window extends over an entire circumference of the shaft in a circumferential direction of the shaft, and
the second mirror is disposed on the inner surface of the shaft such that the second mirror extends over an entire inner circumferential surface of the shaft in the circumferential direction, located distal to the distal end of the lateral emission window.

3. The light therapy diagnostic device according to claim 1, further comprising a circumferential rotating member, wherein
the circumferential rotating member is connected to a proximal part of the optical waveguide such that the optical waveguide is rotatable by rotating the circumferential rotating member in a circumferential direction of the shaft.

4. The light therapy diagnostic device according to claim 1, wherein
the optical waveguide comprises a first core, a second core disposed on the first core, and a clad disposed on the second core, and
a refractive index n1 of the first core, a refractive index n2 of the second core, and a refractive index n3 of the clad satisfy the relationship of $n1>n2>n3$.

5. The light therapy diagnostic device according to claim 4, wherein
the optical waveguide further comprises an intermediate clad disposed between the first core and the second core, and
the refractive index n1 of the first core, the refractive index n2 of the second core, and a refractive index n4 of the intermediate clad satisfy the relationship of $n1>n2>n4$.

6. The light therapy diagnostic device according to claim 4, wherein
the optical waveguide has a non-existent area of the clad where the clad does not exist on the second core, and
the lateral emission window is located at a position corresponding to the non-existent area of the clad such that the second light is allowed to be emitted from the optical waveguide toward the lateral direction through the lateral emission window.

7. The light therapy diagnostic device according to claim 4, wherein
the second core has a light diffusion region disposed proximal to the first mirror such that the second light is allowed to be emitted toward the lateral direction.

8. The light therapy diagnostic device according to claim 7, wherein
the second core contains light diffusing particles in the light diffusion region.

9. The light therapy diagnostic device according to claim 4, wherein
a distal end surface of the first core is inclined with respect to an optical axis of the optical waveguide, and
a metal material, as the first mirror, is disposed on the distal end surface of the first core, such that the first light is allowed to be emitted toward the lateral direction.

10. The light therapy diagnostic device according to claim 1, wherein
a distal end part of the shaft is tapered.

11. The light therapy diagnostic device according to claim 1, further comprising a light source that generates the first light; and
a lens disposed between the light source and the first mirror, wherein
the light source, the lens and the optical waveguide are configured such that the first light is guided through the optical waveguide.

12. The light therapy diagnostic device according to claim 1, further comprising an aberration correction lens disposed distal to the second mirror such that aberration possibly generated by reflection of the first light at the first mirror or the second mirror can be corrected.

13. The light therapy diagnostic device according to claim 1, further comprising a balloon, wherein
the balloon is connected to the lumen of the shaft.

14. A method for operating the light therapy diagnostic device according to claim 1, comprising the steps of:
guiding the first light to the optical waveguide;
guiding the second light to the optical waveguide to emit the second light from the lateral emission window, after guiding the first light to the optical waveguide; and
guiding the first light to the optical waveguide, after emitting the second light from the lateral emission window.

15. The light therapy diagnostic device according to claim 1, further comprising at least one light source for generating the first light and the second light, wherein
the light source and the optical waveguide are configured such that the first and second lights are guided through the optical waveguide, and
a wavelength of the second light is different from a wavelength of the first light.

16. The light therapy diagnostic device according to claim 15, wherein
the wavelength of the first light is from 1.3 µm to 1.8 µm, and
the wavelength of the second light is from 0.64 µm to 0.72 µm.

* * * * *